United States Patent [19]

Greco et al.

[11] Patent Number: 5,008,420

[45] Date of Patent: Apr. 16, 1991

[54] NOVEL SPINEL PRECURSORS

[75] Inventors: Carl C. Greco, Garnerville, N.Y.; Kelly B. Triplett, Stamford, Conn.

[73] Assignee: Akzo nv, Arnhem, Netherlands

[21] Appl. No.: 584,549

[22] Filed: Sep. 18, 1990

[51] Int. Cl.[5] .......... C07F 5/06

[52] U.S. Cl. .......... 556/182; 556/181

[58] Field of Search .......... 556/182

[56] References Cited

FOREIGN PATENT DOCUMENTS 3091392 9/1986 Japan .......... 556/182

*Primary Examiner*—Arthur C. Prescott
*Assistant Examiner*—Profirio Nazario
*Attorney, Agent, or Firm*—Richard P. Fennelly; Louis A. Morris

[57] ABSTRACT

Novel precursors for forming spinel upon oxidation or evaporation from solution can be formed by reaction of an alkylaluminum alkoxide with a magnesium alkoxide to yield an organoaluminum-magnesium alkoxide coordination compound or complex having a molar ratio of aluminum to magnesium of substantially 2:1.

12 Claims, No Drawings

NOVEL SPINEL PRECURSORS

BACKGROUND OF THE INVENTION

It is known to prepare spinel ($MgAl_2O_4$) using alkoxide precursors. For example, U.S. Pat. Nos. 3,761,500 and 3,786,137 to I. M. Thomas and M. Suguira et al., Yogyo-Kyokai-Shi 92 [11] 1984, 605-611 describe the formation of magnesium di-aluminum alkoxide precursors to spinel.

More recently, Y. Takahashi et al., J. Crystal Growth 74 (1986) 409-415 describe formation of a magnesium aluminum double isopropoxide by reaction of magnesium and aluminum metal with isopropanol.

U.S. Pat. Nos. 4,835,298 and 4,946,976 to J. F. Terbot et al. relate to ternary alkoxide formulations but indicate that magnesium alkoxide and aluminum alkoxide are believed to complex forming a homopolar alkoxide consisting of two aluminum atoms, one magnesium atom and eight —OR groups. Col. 4, lines 24-32 of the '298 patent depicts the structure for this complex.

DESCRIPTION OF THE INVENTION

The present invention relates to alkylaluminum alkoxide-magnesium alkoxide coordination compounds containing an amount of aluminum to magnesium, on a molar basis, which is substantially 2:1 so that they are useful as spinel precursors. These coordination compounds (or complexes) are formed by the reaction of an alkylaluminum alkoxide and a magnesium alkoxide.

The alkylaluminum alkoxide which is used to for the instant spinel precursors is unlike those used in the references discussed above which were aluminum alkoxides, not containing an aluminum to alkyl bond of the general formula $Al(OR)_3$, with R being alkyl. In contrast, the alkylaluminum alkoxides used herein have either one or two aluminum to alkyl bonds and at least one oxygen atom in the aluminum alkoxide moiety and are of the formula $AlR_n(OR)_{3-n}$, with n being either 1 or 2, with R preferably being alkyl of from 1 to 8 carbon atoms, most preferably from 1 to 4 carbon atoms.

The term "magnesium alkoxide" as used herein is meant to encompass conventional magnesium alkoxides of the formula $Mg(OR)_2$, where R is lower alkyl, preferably containing from 1 to 4 carbon atoms, as well as magnesium beta-diketonate compounds, e.g., magnesium acetylacetonates.

These coordination compounds can be made by first dissolving the aluminum compound in an appropriate nonpolar organic solvent, such as a hydrocarbon solvent , e.g., toluene or xylene. The magnesium alkoxide, which is insoluble as a rule in such a solvent, is then added thereto and the resulting mixture is refluxed to dissolve the magnesium compound forming the desired coordination compound or complex. The presence of the final desired product can be confirmed by infrared spectroscopy.

The proposed structure for these coordination compounds is as follows when a dialkylaluminum monoalkoxide and a conventional magnesium alkoxide are reacted:

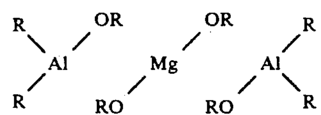

where R is alkyl.

When a monoalkylaluminum dialkoxide is used with a conventional magnesium alkoxide, the following proposed structure results:

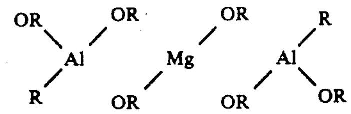

where R is alkyl as previously defined.

The spinel product ultimately desired can be produced by simply evaporating the solvent after the foregoing reflux reaction has been run. Alternatively, the reaction mixture can be hydrolyzed by the addition of water. The solution containing the desired coordination compound can be used to form coatings for use in catalyst, electronic, and structural applications. Conversion to coatings via direct application of the solution by spraying or dipping, followed by hydrolysis and curing is envisioned. Alternatively, the precursors can be first converted to powders which can then be converted to coatings through conventional thermal spray techniques such as plasma spray.

EXAMPLE 1

This illustrates preparation of a coordination compound of the formula $[(C_2H_5)_2AlOC_2H_5]_2Mg(OC_2H_5)_2$.

Into a 500 ml, three-neck flask, was added 28.9 gm of diethylaluminum ethoxide (0.223 mole) in 250 cc of toluene. With vigorous stirring, 12.7 gm of magnesium ethoxide (0.111 mole) was added. The resulting slurry (magnesium ethoxide is insoluble in organic solvents) was heated to reflux. The reaction mixture was refluxed for six hours during which time most of the magnesium ethoxide had gone into solution and had reacted with the aluminum compound. The reaction mixture was cooled to room temperature and was filtered. The filtrate was distilled to constant weight. A colorless solid remained (32 gm, 77% of theory) and was collected as the desired product.

Infrared analysis (IR) was in agreement with the proposed structure. Thermogravimetric analysis (TGA) showed the product to have a sharp decline in weight between 100° C. and 300° C. After 400° C. only 28.2% of the sample remained.

EXAMPLE 2

This illustrates the preparation of a coordination compound of the formula $[C_2H_5Al(OC_2H_5)_2]_2Mg(OC_2H_5)_2$.

The same procedure was used as was employed in Example 1 except that the ethylaluminum diethoxide was prepared in situ by reacting 15 gm of triethylaluminum (0.13 mole) with 12 gm of ethanol (0.26 mole) in 300 cc of toluene. Then, 7.4 gm of magnesium ethoxide (0.065 mole) was added. A colorless sticky solid remained and was collected as the product. The yield was 16.8 gm (64% of theory) and was shown by IR to be the desired product. TGA analysis showed a sharp decline in weight between 200° C. and 300° C. The remaining residue was only 19.3% after 400° C.

The TGA analysis for Examples 1 and 2 were comparable to the known compound $MgAl_2(OC_2H_5)_8$ in terms of weight loss per temperature change. This means that these two compounds have potential as volatile precursors for MOCVD applications.

EXAMPLE 3

This illustrates the preparation of a coordination compound of the formula $C_2H_5Al(OC_2H_5)_2]Mg(OC_5H_7)_2$.

The same procedure was employed as in Example 2 except that 14.5 gm of magnesium acetylacetonate (0.065 mole) was used instead of magnesium ethoxide. The yield of desired product was 29.3 gm (88%) and was shown by IR to be the desired product. TGA analysis showed a slow decline in weight between the temperature of 200° C. to 550° C. where only 62.6% of the material was lost. The residue weight was 37%.

EXAMPLE 4

This illustrates the preparation of a coordination compound of the formula $[(C_2H_5)_2AlOC_2H_5]_2Mg(OC_5H_7)_2$.

The same procedure was used as was used in Example 1 except that magnesium acetylacetonate was used as a reactant. The yield of product was 31 gm (95% of theory). TGA analysis showed a slow decline in weight between 100° C. and 550° C. where only 60% of the sample was lost.

EXAMPLE 5

This illustrates conversion of the magnesium-aluminum compound of Example 1 to spinel.

Ten grams of the product from Example 1 was dissolved in 50 cc of toluene. This solution was allowed to evaporate to dryness in air. A solid remained which was heated in a furnace for two hours at 1100° C. X-ray diffraction (XRD) analysis showed the resulting sample to be essentially pure spinel ($MgAl_2O_4$).

EXAMPLE 6

The same procedure used in Example 5 was followed except the product in Example 4 was converted to spinel. XRD analysis showed this sample to also be essentially pure spinel.

We claim:

1. An alkylaluminum alkoxide-magnesium alkoxide coordination compound containing an amount of aluminum to magnesium such that the molar ratio of aluminum to magnesium is substantially 2:1.

2. A compound as claimed in claim 1 of the formula

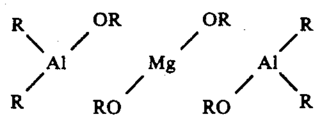

where R is alkyl.

3. A compound as claimed in claim 1 of the formula

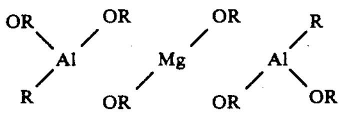

where R is alkyl.

4. A compound as claimed in claim 2 where R is alkyl containing from 1 to about 8 carbon atoms.

5. A compound as claimed in claim 3 where R is alkyl containing from 1 to about 8 carbon atoms.

6. A compound as claimed in claim 4 where R is $C_1$ to $C_4$ alkyl.

7. A compound as claimed in claim 5 where R is $C_1$ to $C_4$ alkyl.

8. A compound as claimed in claim 1 where R is alkyl containing from 1 to about 8 carbon atoms.

9. A compound as claimed in claim 8 where R is $C_1$ to $C_4$ alkyl.

10. A compound as claimed in claim 1 where R is ethyl.

11. A compound as claimed in claim 2 where R is ethyl.

12. A compound as claimed in claim 3 where R is ethyl.

* * * * *

UNITED STATES PATENT AND TRADEMARK OFFICE
CERTIFICATE OF CORRECTION

PATENT NO. : 5,008,420

DATED : April 16, 1991

INVENTOR(S) : Carl C. Greco and Kelly B. Triplett

It is certified that error appears in the above-identified patent and that said Letters Patent is hereby corrected as shown below:

Col. 1, lines 62-68 and in Claim 2, change the formula to read:

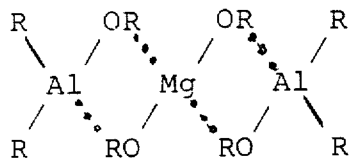

Col. 2, lines 5-10 and in Claim 3, change the formula to read:

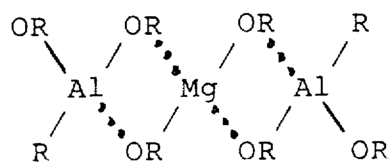

Signed and Sealed this

Eleventh Day of August, 1992

Attest:

DOUGLAS B. COMER

Attesting Officer

Acting Commissioner of Patents and Trademarks